11/18/80 XR 4,233,988

United States Patent [19] [11] 4,233,988
Dick et al. [45] Nov. 18, 1980

[54] HIGH RESOLUTION ROTATING HEAD ULTRASONIC SCANNER

[75] Inventors: Donald E. Dick, Boulder; Robert L. Metz, Superior; D. Scott RoJohn, Boulder; Raymond D. Elliott, Denver, all of Colo.

[73] Assignee: Life Instruments Corporation, Boulder, Colo.

[21] Appl. No.: 922,185

[22] Filed: Jul. 5, 1978

[51] Int. Cl.³ .............. A61B 10/00

[52] U.S. Cl. .............. 128/660; 73/633; 73/642

[58] Field of Search .............. 128/660-663; 73/618-626, 633, 642; 367/104-105, 119-121

[56] References Cited

U.S. PATENT DOCUMENTS

| | | | |
|---|---|---|---|
| 3,247,709 | 4/1966 | Gordon | 73/621 |
| 3,308,652 | 3/1967 | Appell et al. | 73/626 |
| 3,480,002 | 11/1969 | Flaherty et al. | 128/660 |
| 3,886,490 | 5/1975 | Green | 340/5 MP |
| 4,012,952 | 3/1977 | Dory | 367/105 |
| 4,016,751 | 4/1977 | Kossoff | 73/626 |
| 4,034,744 | 7/1977 | Goldberg | 128/660 |
| 4,075,883 | 2/1978 | Glover | 128/660 |
| 4,078,435 | 3/1978 | Kossoff et al. | 128/660 |
| 4,094,306 | 6/1978 | Kossoff | 128/660 |
| 4,161,121 | 7/1977 | Zitelli et al. | 73/626 |

OTHER PUBLICATIONS

Fry, E. K. et al., "A Combined Clinical & Research Approach to the Problem of UTS Visualization of the Breast," UTS in Med., vol. 1, Plenum Publ. 1975.

Kossoff, G. et al., "Octoson: A New Rapid Multi-Transducer General Purpose Water-Coupling Echoscope," Conference: Proceedings of the 2d Europ. Cong. on UTS in Med., Munich, Germany, 12-16, May 1975, pp. 90-95.

Kisslo, J. et al., "A Phased Array UTS System for Cardiac Imaging," Conference: Proc. of the 2nd Europ. Congress on UTS in Med., Munich, Germany, 12-16 May 1975, pp. 67-74.

*Primary Examiner*—Robert W. Michell
*Assistant Examiner*—Francis J. Jaworski
*Attorney, Agent, or Firm*—Sheridan, Ross, Fields & McIntosh

[57] ABSTRACT

An improved high resolution rotating head ultrasonic scanner is provided for use in an ultrasonic scanning subsystem of an ultrasonic breast scanning system. The scanning subsystem of the breast scanning system includes a pair of high resolution ultrasonic rotating scanning heads mounted on a transport mechanism. A scan is conducted by moving the transport mechanism while the scanning heads rotate so that a series of parallel uniformly spaced cross-sectional scans of the tissue of the breast are conducted from the inferior to the superior border of the breast. Each scanning head has three ultrasonic transducers uniformly spaced around its perimeter. The focal ranges of the transducers of a given scanning head are chosen so that a sector scan conducted by each head is divided into slightly overlapping zones with the depth of each zone corresponding to the focal range of one of the transducers on each scanning head. The angular velocity and phase of the scanning heads are controlled so that during one revolution of the scanning heads each transducer of each head conducts a sector scan primarily through its zone. However, only one such transducer will conduct such a scan at any one time.

26 Claims, 11 Drawing Figures

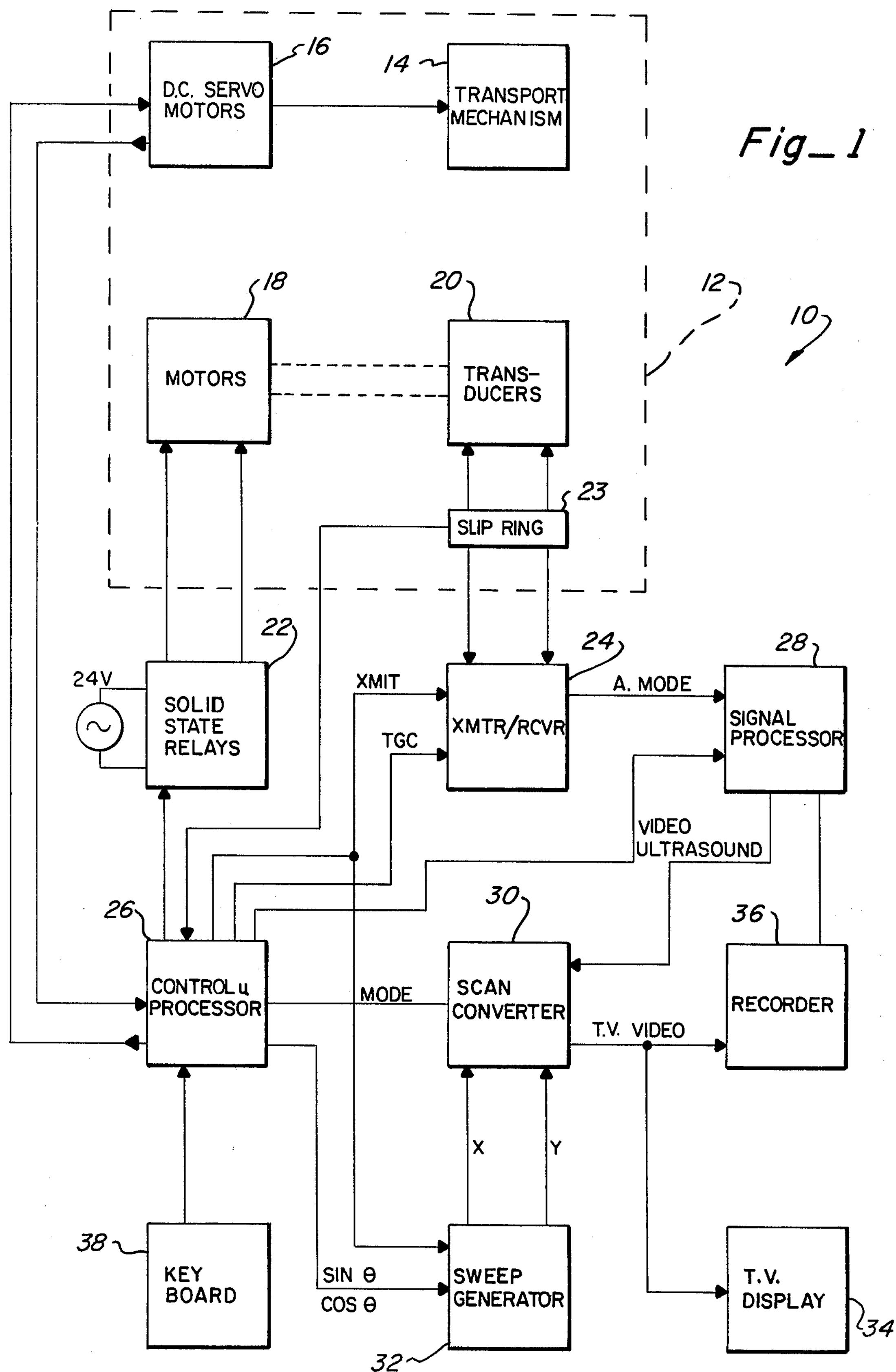
Fig_1
D.C. SERVO MOTORS
16
14
TRANSPORT MECHANISM
18
20
12
10
MOTORS
TRANS-DUCERS
23
SLIP RING
22
24V
SOLID STATE RELAYS
24
28
XMIT
TGC
XMTR/RCVR
A. MODE
SIGNAL PROCESSOR
VIDEO ULTRASOUND
26
30
36
CONTROL μ PROCESSOR
MODE
SCAN CONVERTER
T.V. VIDEO
RECORDER
X
Y
38
KEY BOARD
SIN θ
COS θ
SWEEP GENERATOR
32
T.V. DISPLAY
34

81
88
82
4
4
86
90
91
84
79
40
α
92
44
42
46
69
68

78
73
72
77
71b
71a
93
94
74
75
70
48
76b
96
95
97
66a
66b
67a
64d
64c
62
64a
64b
67b 60
55
55
54
61
58
53
51
57
3
50
40
42
76b
44
76a 52
48
3
59
56
59

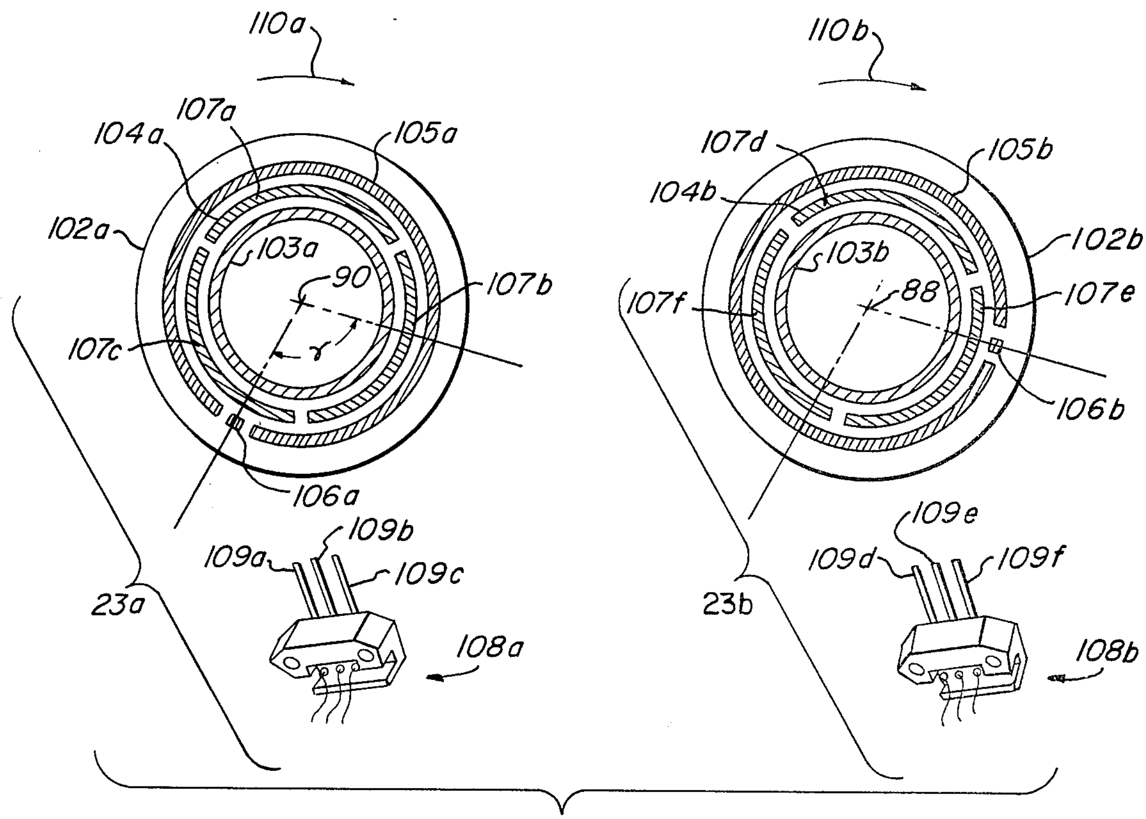
Fig_6
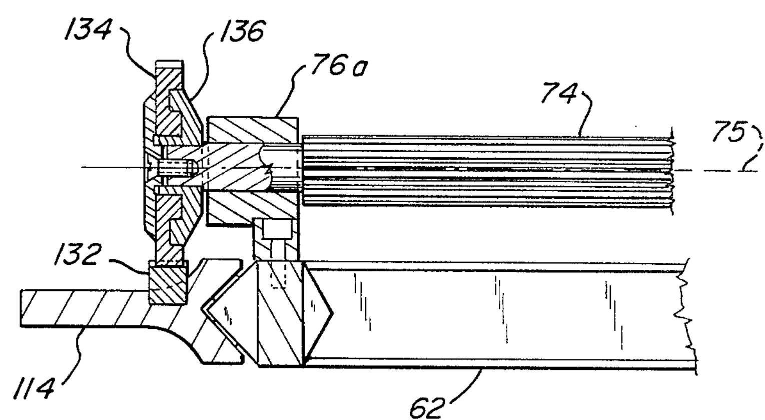
Fig_10

HIGH RESOLUTION ROTATING HEAD ULTRASONIC SCANNER

BACKGROUND OF THE INVENTION

1. Field of the Invention

This invention is in the field of medical ultrasonic diagnostic equipment and more particularly relates to improved high resolution rotating head ultrasonic scanners particularly adapted for use in the scanning subsystem of an ultrasonic breast scanning system.

2. Description of the Prior Art

There are statistical data up to and including the early 1970's to the effect that there has been essentially no change in the death rate from cancer of the breast of American women. Early detection is the most significant factor in improving the probability of survival of a patient with breast cancer.

The primary methods of detecting cancerous growths within the breast are manual palpation, X-ray examination, which includes mammography and xeroradiography and thermography. Each of the foregoing techniques has its advantages but each has serious limitations with respect to its use for the early detection of breast carcinoma. Fry, E. K., Kossof, G., Hindman, H. A., Jr., The Potential of Ultrasonic Visualization for Detecting of Abnormal Structure Within the Female Breast, IEEE, Ultrasonic Symposium Proceedings, pp. 25–30, 1972.

In the early 1950's the potential for using ultrasound visualization systems to detect breast carcinoma was demonstrated. Some of the advantages of ultrasonic visualization techniques are that ultrasound is noninvasive, can be externally applied, is nontraumatic and is safe at the acoustical intensities and duty cycles encountered in existing diagnostic equipment. While the potential of ultrasound visualization of breast tissue has been recognized and the need for ultrasonic breast scanning instruments or systems is also recognized, the development of such instruments for clinical use in screening large numbers of patients has not heretofore been accomplished.

In order to detect as early as possible breast carcinoma, or precancerous conditions, the resolution of visualizations of the tissue scanned must be good. Such resolution is improved by not distorting the breast tissue during the examination. One way of accomplishing this is to have the patient's breasts freely floating in a liquid such as water, which liquid serves as the coupling medium for transmitting ultrasonic energy from a transducer to the tissue and reflections from transmitted pulses of such energy from sources within the tissue due primarily to changes in speed of transmission of the sound in the tissue back to the transducer. In addition, such an instrument should not cause the patient to suffer any discomfort and should require a minimum of time to prepare the patient for examination. Sucn an instrument should conduct an examination quickly and reliably without requiring highly skilled technicians or operators to operate the instrument.

In conducting an ultrasonic examination of breast tissue, it is important that the liquid level in the examination tank in which the patient's breasts are immersed be maximized so that the tissue under the patient's arms can be examined to detect the possibility of the spread of breast cancer. Prior art ultrasonic breast scanners in which the patient's breasts are immersed in a liquid have tried to confine the liquid by a liquid tight seal between the patient and the tank. A problem with such prior art breast scanners is that they have not been successful in minimizing the amount of liquid escaping from the examination tank during an examination.

Prior Art Statement

The following references are submitted under the provisions of 37 CFR 1.97(b):

Patents:

U.S. Pat. No. 3,480,002 Flaherty et al

U.S. Pat. No. 4,034,744 Goldberg

Publications:

Fry, E. K. et al., "A Combined Clinical and Research Approach to the Problem of Ultrasound Visualization of the Breast," Ultrasound in Medicine, Volume 1, D. N. White, ed. Plenum 1975, pp. 309–320.

Flaherty et al, U.S. Pat. No. 3,480,002, discloses an ultrasonic system especially designed for breast examination. A single transducer is mounted on a carriage so that the transducer can be moved relative to the patient while the transducer is oscillated to conduct a scan in one plane through a patient's breast. The transducer is immersed in water within a water bag which is placed over one or both of the patient's breasts as illustrated in FIGS. 1 and 2. As an alternative, in FIG. 5, the patient is prone on a table through which her breasts may extend into a tank filled with water within which the transducer is positioned. Echoes received by the transducer are converted to electrical signals and processed to produce images, or visualizations, of the scanned tissue on a cathode ray tube.

Goldberg, U.S. Pat. No. 4,034,744, discloses an ultrasonic sector scanning system in which a scanner is provided with a rotor which in turn is provided with four transducers spaced around the periphery of the rotor which rotor is located within a spherical portion 109. The transducers are mounted so that they are perpendicular to the axis of rotation of the rotor. In conducting a scan the window 83 in portion 109 is placed against the tissue to be visualized.

The publication by Fry, E. K., Fry, F. J., Sanghvi, N. T., and Heimburger, R. F., entitled "A Combined Clinical and Research Approach to the Problem of Ultrasound Visualization of the Breast," Ultrasound in Medicine, Vol. 1, D. N. White, ed. Plenum, 1975, pp. 309–320, has a good discussion of the state of the art and describes an ultrasonic breast scanning system which uses a single wide apertured focused transducer in providing each image of the tissue scanned. Improved resolution of the images produced is accomplished with the aid of a digital computer which allows segmented construction of echograms by moving the transducer relative to the patient's skin and controlling receiver gain to select the depth range of interest.

SUMMARY OF THE INVENTION

The present invention provides an improved high resolution rotating head ultrasonic scanner particularly adapted for use in a scanning subsystem of an ultrasonic breast scanning system which is provided with a pair of such ultrasonic scanners with each scanner having a rotating scanning head. A plurality of wide apertured focused ultrasonic transducers are mounted on each head. The scanners are mounted on a transport assembly and scanners and transport assembly make up the scanning subsystem. The scanning subsystem is designed to operate while immersed in a liquid such as water in an examination tank which is positioned within an overflow tank. The transport assembly has a pair of straight rails which are substantially parallel to each other. A truss or bridge runs on the rails. The bridge has a longitudinal axis which is normal to the direction of the rails. A movable carriage is mounted on the bridge to move in a direction parallel to the longitudinal axis of the bridge. The bridge and carriage are movable so that the carriage can be placed at any point within a predetermined area and substantially bounded by said rails. Pulleys are mounted on the rails and bridge and a pair of flexible cables are connected around them and to the carriage to control the direction and velocity of movement of the carriage and the bridge or both. Means for applying power to selected ones of the pulleys or to the flexible cables to control the movement of the carriage and bridge are provided. A flipping mechanism is incorporated into the movable carriage to orient the scanning heads so that the beams of focused ultrasonic energy from each transducer will be substantially normal to the surface of the breast being scanned.

The scanners are mounted at the end of a pair of fixed arms which are pivotally mounted on the carriage. Each scanner has a scanning head mounted for rotation on its body about an axis of rotation which is substantially parallel to the longitudinal axis of the bridge. Each head has a plurality of ultrasonic wide apertured focused transducers and each transducer is adapted to be connected to an ultrasonic transmitter and receiver in sequence. Each transducer of a given scanning head has a different focal range. The transducers are connected to the transmitter receivers so that they conduct overlapping sector scans with each sector being divided into slightly overlapping zones, the width of each zone substantially corresponding to the focal ranges of the transducers of each scanning head. The transducers of each scanning head are uniformly distributed around the perimeter of its scanning head and so that the axis of its focused beam of ultrasonic energy when produced is substantially perpendicular to the axis of rotation of the scanning head on which they are mounted and substantially lie in the same plane. A motor is mounted in the body portion of each scanner to rotate the scanning heads at the same predetermined angular velocity in the same direction and at a predetermined phase angle, or relationship, to one another to provide overlapping sector scans of tissue which tissue is substantially uniformly distributed with respect to the perpendicular bisector of the line between the axes of rotation of the scanning heads. The scanners are constructed and controlled so that only one transducer of any one scanning head will be operationally connected to the transmitter/receiver at any one time and each transducer will be so connected to the transmitter/receiver once during each revolution of each scanning head.

The transport mechanism is controlled to position the scanners so that they are substantially equidistantly spaced from the breast to be scanned, so that the perpendicular bisector of a line between the axes of rotation of the scanning heads of the scanners passes through the nipple at an angle substantially normal to the patient's rib cage with the result that the beams of focused ultrasonic energy from each transducer will be substantially normal to the surface of the breast being scanned.

It is therefore an object of this invention to provide an improved high resolution rotating head ultrasonic scanner.

It is another object of this invention to provide in an ultrasonic breast scanning system an improved scanning subsystem which provides images of a section of tissue of significantly greater resolution.

It is yet another object of this invention to provide an improved scanning subsystem for a medical examination system for conducting the screening of large numbers of patients to detect at the earliest time possible breast cancer or precancerous conditions of the breast.

It is still another object of this invention to provide an improved scanning subsystem for an ultrasonic breast scanner which produces higher resolution visualization of breast tissue without distorting the tissue being scanned.

It is a further object of this invention to provide an ultrasonic breast scanner system in which the escape of liquid from the system is substantially prevented.

It is a still further object of this invention to provide an improved transport mechanism for the scanners of an ultrasonic breast scanner system which properly orients the scanners.

It is yet another object of this invention to provide an improved ultrasonic breast scanning system which does not cause discomfort to the patient being examined, does not require a skilled operator, and the positioning of the scanning heads and the carriage on which the scanning heads are mounted relative to the patient is easily, quickly and accurately accomplished for patients of substantially all sizes.

It is a further object of this invention to provide a scanning subsystem for an ultrasonic breast scanning system which permits the examination to be connected quickly while producing high resolution visualizations of the tissue scanned so that large numbers of patients can be examined in a relatively short period of time.

BRIEF DESCRIPTION OF THE DRAWINGS

Other objects, features and advantages of the invention will be readily apparent from the following description of certain preferred embodiments thereof, taken in conjunction with the accompanying drawings, although variations and modifications may be effected without departing from the spirit and scope of the novel concepts of the disclosure, and in which:

FIG. 1 is a block diagram of an ultrasonic breast scanning system with which the scanning subsystem of the present invention can be used;

FIG. 6 is a schematic view of the slip ring assembly of the scanners;

FIG. 10 is an enlarged fragmentary view of the mechanism for providing power to the orienting portion of the transport mechanism.

DETAILED DESCRIPTION OF THE INVENTION

Figure 3:
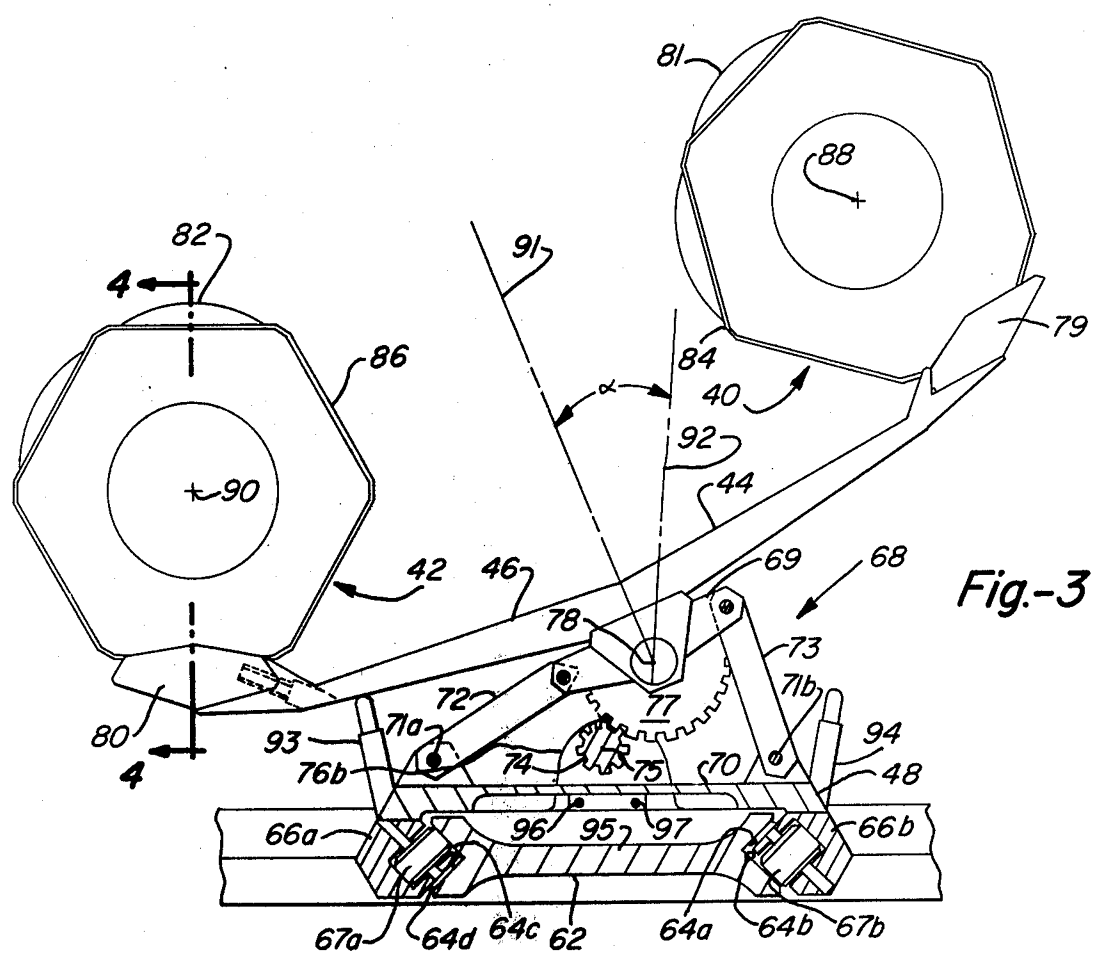
FIG. 3 is an enlarged section taken on line 3—3 of FIG. 2.

In FIG. 1, the subsystems and components of some of the subsystems of ultrasonic breast scanning system 10 are illustrated. Some of the components of the scanning subsystem 12 are also illustrated in FIG. 1 such as the transport mechanism 14 and the motor, or motors, 16 for the transport mechanism. In FIG. 1 motors 18 that drive or rotate the ultrasonic transducers 20 of scanning subsystem 12 are illustrated.

The solid state relays 22 are used to control the energization of motors 18 and in particular to control the phase of the scanning heads which are not illustrated in FIG. 1 on which the ultrasonic transducers 20 are mounted as will be described later. Transducers 20 which are in a preferred embodiment wide apertured focused ultrasonic transducers are operationally connected by slip rings 23 to a conventional ultrasonic transmitter/receiver 24.

System 10 operates in a pulse echo mode with transmitter/receiver 24 producing pulses of electrical energy. In a preferred embodiment the pulses produced by transmitter/receiver 24 have a pulse repetition rate of 3.4133 kHz with each pulse having a pulse width of 0.1 μsec. The frequency of the ultrasound waves produced by transducers 20 in response to the electrical pulses applied to them from transmitter/receiver 24 is in the range of from 1 to 10 MHz in the preferred embodiment. The pulses of electrical signals produced by transmitter/receiver 24 are applied to one of the ultrasonic transducers 20 which in response to the electrical signals applied to it produces acoustic energy having a frequency depending on the construction of the transducer and the material used. During periods of time between acoustic pulses, echoes produced by the reflections of the transmitted pulses of acoustic energy primarily from the interfaces within tissues having different acoustical impedances are received by the transducer transmitting the pulse in the preferred embodiment and are converted by that transducer to electrical signals, the amplitudes of the electrical signals produced being a function of the amplitude of the acoustic signals received. The electrical signals from the transducers are applied to transmitter/receiver 24 through slip ring assemblies 23.

Control, including timing, of ultrasonic scanning system 10 is performed by a microcomputer 26 which in the preferred embodiment is a MOS Technology Model 6502. The timing signals used by system 10 are derived from the clock of microcomputer 26 as is well known in the art. Typically the clock is a crystal controlled oscillator together with appropriate frequency dividers to provide signals or pulses of the frequencies needed. Transmitter/receiver 24 produces a transmission pulse, when a transmit signal (Xmit) is applied to transmitter/receiver 24 by controller 26. Control computer 26 beginning at the time it produces an Xmit signal will produce a time gain control signal (TGC) which varies the gain of the receiver of transmitter/receiver 24 to compensate for the rapid attenuation of acoustic signals reflected back to a transducer 20 as a function of time as is well known in the art. The echoes received by a transducer 20 are converted or made into electrical signals, an A mode signal which is applied to signal processor 28. An A mode signal is one suitable for being applied to a time base oscilloscope for displaying the amplitudes of the received echoes. Signal processor 28 converts the A mode signals from receiver 24 into ultrasonic video or intensity modulated signals.

The ultrasonic video signals from processor 28 are applied to a conventional scan converter 30 to which also is applied signals "X" and "Y" from sweep generator 32. "X" and "Y" are the coordinates of the ultrasonic video signal at any given instant in time so that an intensity or Z axis modulated display of the sources of the echoes received by a transducer or transducers can be mapped out as a two-dimensional cross-section view.

The Xmit signal from controller 26 which ultimately causes a transducer 20 to produce a pulse of acoustic energy is also applied to sweep generator 32 so that the distance "r" of the source of an echo received by a transducer can be determined since $r=c\ t/2$ where c equals the velocity of sound in the medium. The sine, cosine functions of $\theta$, the angle of the scanning transducer at any given time is supplied to sweep generator 32 by controller 26 using a table of the values of sin $\theta$, cos $\theta$ which are stored in the memory of computer 26. Knowing r, sin $\theta$ and cos $\theta$, sweep generator 32 calculates X and Y the coordinates of the ultrasound video signal applied to scan converter 30 at time t.

Scan converter 30 accepts information in one mode such as random X-Y patterns which are intensity modulated by the ultrasound video signals from signal processor 28 and converts this information into video signals, for example, suitable for display on conventional TV display 34 on a real time basis. The video signals from scan converter 30 can be stored on a video recorder 36 so that the video signals of any or all images so recorded can be reproduced and displayed at a later time on TV display or monitor 34, for example. Keyboard 38 is used by the operator of the ultrasonic scanning system 10 to apply commands and to supply data to system 10.

Figure 2:
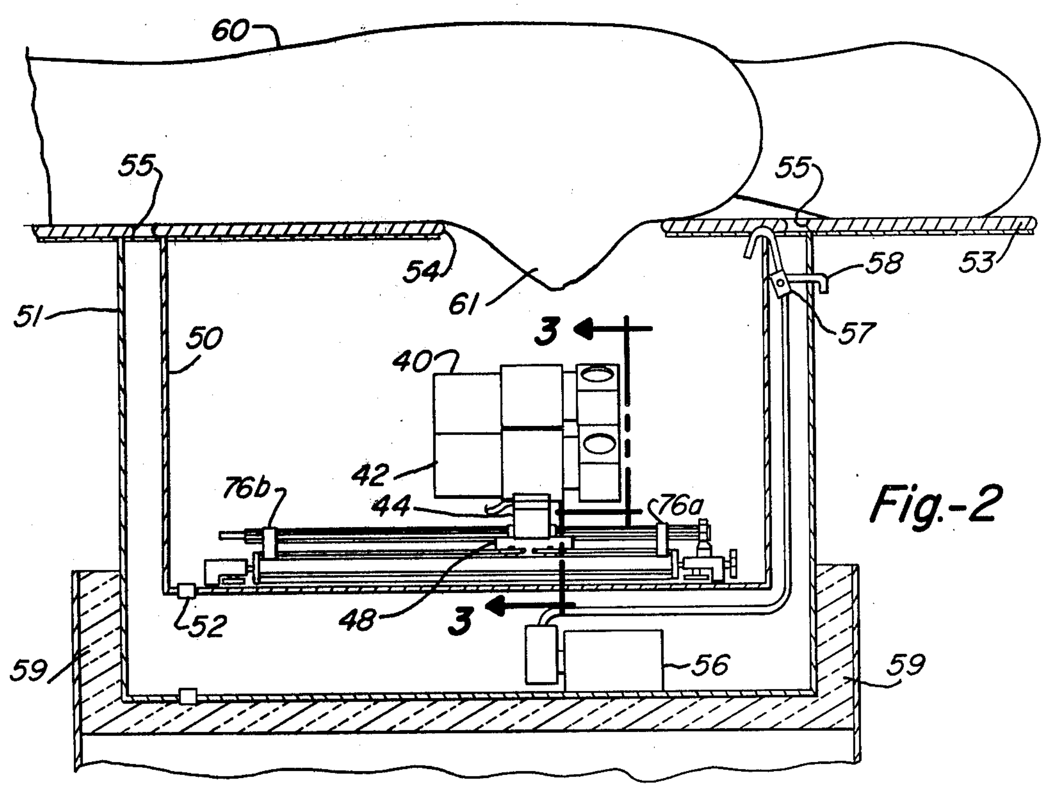
FIG. 2 is a schematic side elevation illustrating the position of a patient relative to the scanning subsystem during an examination.

In FIG. 2 scanners 40, 42 of scanning subsystem 12 can be seen. Scanners 40, 42 are mounted on a pair of supporting arms 44, 46, only arm 44 is seen in FIG. 2, which arms are mounted on a movable carriage 48 of the transport mechanism 14. Scanning subsystem 12 is located in examination tank 50. Examination tank 50 is located within overflow tank 51. The capacity of tank 51 is such that if conventional valve 52 in the bottom wall of examination tank 50 is opened all the liquid in tank 50 can drain into overflow tank 51. Overlying tanks 50, 51 is an examination table 53 which is provided with an examination opening 54. A drainage opening 55 is formed in table 53 substantially surrounding examination tank 50 so that liquid from examination tank 50 that overflows the top of examination tank 50 will flow into and be collected in overflow tank 51. A submersible pump 56 is positioned in the bottom of overflow tank 51. Depending on the position of valve 57, pump 56 will pump liquid from overflow tank 51 into examination tank 50 so that the level of the liquid, degassed water in a preferred embodiment, within tank 50 will be maintained at the maximum level so that the underarm areas of a patient can be examined to determine if breast cancer has spread to this part of a patient's body; or to drain spigot 58 to empty both examination tank 50 and overflow tank 51. The lower portion of overflow tank 51 can be covered with insulation 59 to minimize the loss of heat from liquid contained therein. A patient 60 lies prone on the upper surface of table 53 with her breasts 61 freely floating in a liquid which substantially fills examination tank 50. In the preferred embodiment the liquid is water which is maintained substantially at a temperature which is not uncomfortable to the patient, a temperature in the range of 37° C., for example. The benefits of having the patient's breasts immersed in water in this manner are that there is no distortion of the outer or internal structures of the breasts and the liquid filling tank 50 provides a good coupling medium for ultrasonic sound from the transducers 20 of scanners 40, 42 to the tissue to be visualized and, equally as well, a good medium for the reflected signals, or echoes, from the tissue scanned to the transducer 20 which of course enhances the resolution of the images of the tissue, or their visualization.

The location of examination tank 50 within overflow tank 51 and providing drainage opening 55 in the examination table 53 so that liquid from examination tank 50 can flow into overflow tank 51 has solved the prior art problem of trying to minimize the amount of liquid escaping from the examination tank while maintaining the level of the liquid in the tank at the highest possible level to assure that the examination is as thorough and complete as possible. The overflow tank eliminates the need for water tight seals between the patient and the top of the examination tank and avoids the loss of substantial quantities of liquid which liquid is expensive both to heat and to degas.

In FIG. 3 additional details of carriage 48, scanners 40, 42 and arms 44, 46 are illustrated. Bridge, or truss, 62 is provided with substantially planar surfaces 64*a, b, c, d* which intersect to form a groove within which a wedge-shaped portion 66*a, b* of carriage 48 project. A plurality of rollers 67*a*, 67*b* are mounted in wedges 66*a, b*, preferably three in each wedge 66*a* and 66*b* for a total of six. Rollers 67 roll on surfaces 64*a, b, c, d* to permit carriage 48 to move smoothly and with little frictional drag along bridge 62.

Arms 44, 46 are mounted on a four-member flipping, or orienting mechanism 68, more particularly top member, or link, 69 which is connected to base member, or link, 70, the portion of carriage 48 between pivots 71*a*, 71*b* by a pair of arms 72, 73. It should be noted that arms 72 and 73 are of substantially equal length. The four links 69, 70, 72 and 73 are pivotally connected together. A pinion gear 74 is mounted for rotation about its longitudinal axis 75 on a pair of shoulders 76*a*, 76*b* on bridge 62. Only shoulder 76*b* is seen in FIG. 3. An orienting gear 77 is fixedly secured to top member 69 and its dimensions are chosen so that the teeth of gear 77 mesh with the teeth of pinion gear 74 so that when pinion gear 74 rotates about its axis of rotation 75, the orientation of top member 69 changes in a predetermined manner.

The relationship between the lengths of arms 72, 73 which in the preferred embodiment are equal and the length of top member 69 and base link 70 as well as the axis of rotation 75 of pinion gear 74 are chosen so that over a substantial angle of movement of top link 69, 45° in the preferred embodiment, or ±22 ½° on either side of vertical, the distance between the center 78 of gear 77 and the axis of rotation 75 of pinion gear 74 is substantially constant. Thus the locus of the point of contact between orienting gear 77 and pinion gear 74 coincides with the perimeter of pinion gear 74 as top member 69 moves through an angle of up to 45°.

Arms 44, 46 are in the preferred embodiment substantially of the same length. At the ends of arms 44, 46 scanner holders, or mounts, 78, 80 removably secure the body portions 81, 82 of scanners 40, 42 to arms 44, 46. The hexagonal scanning heads 84, 86 are rotatably mounted on body portions 81, 82 for rotation about axis of rotation 88, 90.

In FIG. 3 perpendicular bisector 91 of the line connecting the axes of rotation 88, 90 of scanners 40, 42 passes through the center of gear 78 and is at an angle $\alpha$ with respect to vertical axis 92 with $\alpha$ equaling 22½° in the preferred embodiment. Adjustable stop 93 is set to limit $\alpha$ to 22½°. Counterclockwise rotation of pinion gear 74 will cause flipping mechanism 68 to cause top member 69 to be reoriented so that perpendicular bisector 91 will be on the right-hand side of vertical axis 92. Adjustable stop 94 is positioned so that when the bottom surface of arm 44 engages stop 94, $\alpha$ will have a value of −22½° in the preferred embodiment.

A channel 95 is formed in the upper surface of bridge 62. Small diameter flexible cables 96, 97 are attached to carriage 48 by conventional means to cause carriage 48 to slide on, or more relative to, bridge 62 as will be explained below.

Figure 4:
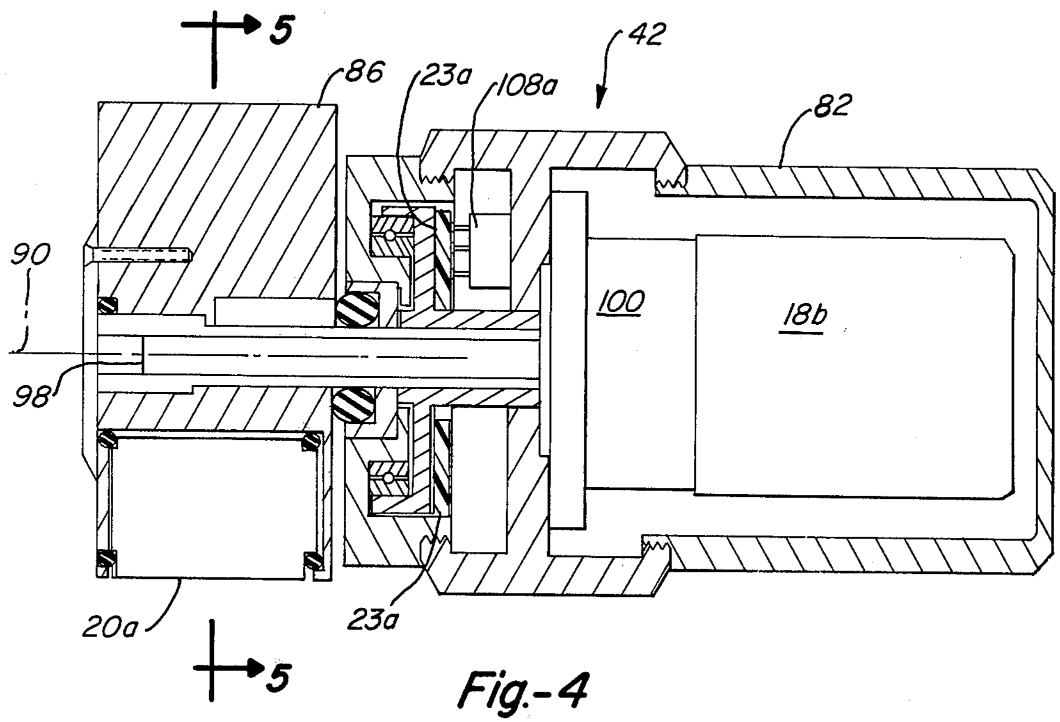
FIG. 4 is a section taken on line 4—4 of FIG. 3.
Figure 5:
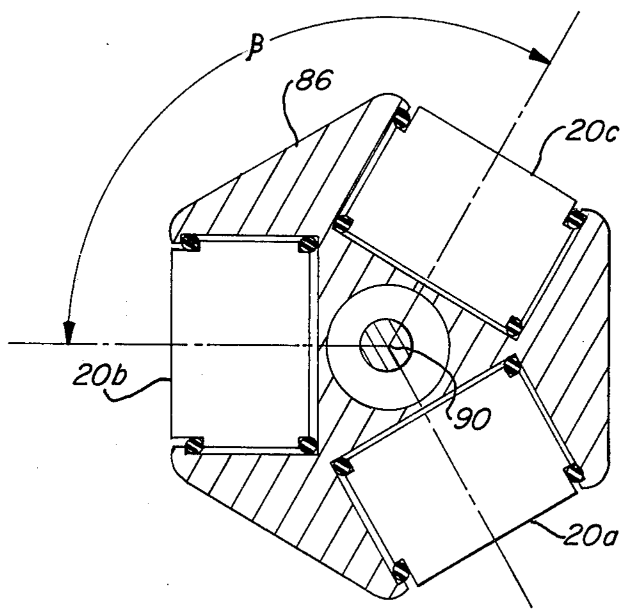
FIG. 5 is a cross-sectional view taken on line 5—5 of FIG. 4.

FIG. 4 is a cross-section of scanner 42. Within the body portion 82 is located motor 18*b* which, in a preferred embodiment, is a 24 volt synchronous AC motor that rotates at 3600 rpm. Motor 18*b* is connected to drive shaft 98 by reduction gears 100, which in the preferred embodiment reduces the rpms of shaft 98 to 100 rpm. As can be best seen in FIG. 5 scanning head 86 has three wide apertured focused ultrasonic transducers 20*a*, *b* and *c* which are uniformly distributed, or positioned, around the perimeter of scanning head 86 with the angle $\beta$ between the axes of the radiation patterns, or beams, of focused ultrasonic energy produced by transducers 20*a, b, c* being 120° in the preferred embodiment, substantially normal to the axis of rotation 90 of scanning head 86. Scanning head 86 is mounted on shaft 98 so that the axis of rotation of shaft 98 coincides with axis 90 with the result that the radiation patterns of transducers 20*a, b, c*, substantially lie in a plane perpendicular to axis 90. To provide an electrical connection between the transducers 20*a, b, c* of scanning head 86, and transmitter/receiver 24, a slip ring assembly 23*a* is provided. Since scanner 42 is operated while immersed in a liquid such as water great care is taken to assure that the interior of housing 82 and scanning head 86 are constructed to prevent the entrance of moisture into the interior of housing 82 and of scanning head 86 particularly around the bearings and where the wires connecting scanner 42 with the rest of the system 10 enter into body or housing 82. In addition a compressed air line is connected to housing 82 so that air at a pressure greater than that of the liquid surrounding housing 82 is present within housing 82.

Since the safety of the patient is paramount, the design of the scanner subsystem is ultraconservative with respect to minimizing the risk of electrical short circuits occurring in any portion of the system and particularly so with respect to the scanning subsystem. To further reduce the hazard, low voltages are used to supply power to subsystems located in examination tank 50 such as 24 volts AC is used to power motors 18*a, b*. The wires which carry electrical power to motor 18*b* and the wires that connect the transducers 20 to transmitter/receiver 24 and the wires for the necessary control signals needed by the scanners 40, 42 or other components of system 10 and the compressed air lines are attached or are connected to the arms, such as arm 46 for scanner 42 and then to the carriage 48 and from carriage 48 they then proceed outside of examination tank 50.

In FIG. 6 slip ring assemblies 23*a* of scanner 42 and 23*b* of scanner 40 are schematically illustrated. Assembly 23*a* has a circular disc 102*a* on which are formed three conductive rings, inner ring 103*a*, transducer ring 104*a* and outer ring 105*a*. Inner ring 103*a* is continuous and is at ground potential. Outer or fiduciary ring 105*a* has a fiducial mark 106*a* which is at ground potential in the preferred embodiment. The balance of outer ring 105*a* is floating; i.e. electrically isolated. Transducer ring 104*a* is divided into three substantially equal sized segments, or arcs, 107*a, b, c*. The central angles determined by arcs 107*a, b, c* are slightly less than 120°. The center of disc 110*a* lies on the axis of rotation 90 of scanning head 86. The wiper arm subassembly 108*a*, which is also illustrated schematically in FIG. 4, is mounted on body portion 82 of scanner 42 so that the wiper arms, or contacts, 109*a, b, c* ride on or contact rings 103*a*, 104*a*, 105*a*. The direction of rotation of scanning head 86 is the direction of arrow 110*a*, or clockwise.

Slip ring assembly 23*b* is similar to assembly 23*a*. It has a disc 102*b* on which are formed three conductive rings 103*b*, 104*b*, 105*b*. Inner ring 103*b* is at ground potential. Fiduciary ring 105*b* has a fiducial mark 106*b* at ground potential. Transducer ring 104*b* is divided into three substantially equal sized segments, or arcs, 107*d, e, f*, with the central angles determined by arcs 107*d, e, f* being slightly less than 120°. The center of disc 102*b* lies on the axis of rotation 88 of scanning head 84. The wiper arm subassembly 108*b* is substantially identical to that of 108*a*. The direction of rotation of scanning head 84 is the direction of arrow 110*b*.

Conductive arcs 107*a, b, c* of slip ring assembly 23*a* are connected to transducers 20*a, b, c*, respectively, and conductive arcs 107*d, e, f* are connected to transducers 20*d, e, f*, respectively. The center conductor, or wiper, 109*b* and 109*e* of wiper arm subassemblies 108*a, b* are connected to transmitter/receiver 24 by conductors that run down arms 44, 46 to carriage 48 and from carriage 48 along the sides of examination tank 50 until they pass out of the top of tank 50, for example. Wiper arms 109*a*, 109*d* are connected to control processor 26, and wiper arms 109*c*, 109*f* are connected to electrical ground by wires which are run substantially parallel to the wires connecting wiper arms 109*b*, 109*e* to transmitter/receiver 24 at least until they leave tank 50.

In FIG. 6 the fiducial marks 106*a*, 106*b* are positioned on fiduciary rings 105*a*, 105*b* so that they have a predetermined angular position with respect to the arcs 107 of transducer rings 104*a*, 104*b* which arcs are electrically isolated from one another. Having fiduciary marks 106*a*, 106*b* with a known relationship to the arcs 107 of transducer rings 104*a*, 104*b* makes it possible to have overlapping sector scans be conducted by the transducers of each scanner head 84, 86 while still making certain that only one transducer 20 is connected to transmitter/receiver 24 at any one time and so that one transducer 20 is connected to transmitter/receiver 24 substantially at all times during each revolution of scanner heads 84, 86 as will be explained later.

Figure 7:
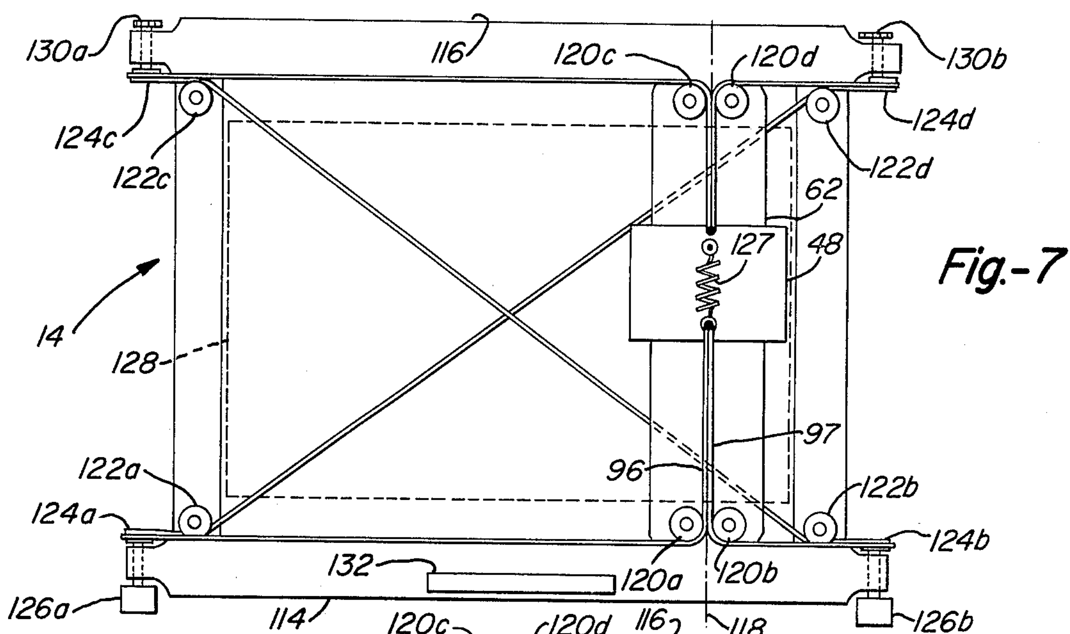
FIG. 7 is a plan view of the transport mechanism of the scanning subsystem.

Referring to FIG. 7 transport mechanism 14 has a pair of rails 114, 116 which are fixedly mounted in examination tank 50. Rails 114, 116 are parallel to each other and are spaced apart a fixed distance and define, or lie in, a plane that is substantially horizontal. Bridge, or truss, 62 is mounted on rails 114, 116 so that bridge 62 can move on rails 114, 116 parallel to them and so that the longitudinal axis 118 of bridge 62 is perpendicular to rails 114, 116. Carriage 48 is mounted on bridge 62 for movement parallel to longitudinal axis 118 of bridge 62. Only an outline of carriage 48 is illustrated in FIG. 7 since carriage 48 was illustrated in greater detail on FIG. 3 and has been described above. In the preferred embodiment bridge 62 and rails 114, 116 are provided with cooperating wedge shaped surfaces similar to the surfaces of bridge 62 and carriage 48 as well as rollers which are not illustrated which permit carriage bridge 62 to move easily on rails 114, 116.

Four bridge pulleys 120*a, b, c, d* are mounted on bridge 62, two substantially at each end of the bridge and the pulleys are so mounted that they are spaced equidistantly from the longitudinal axis 128 of truss 62. Four rail pulleys 122*a, b, c, d* are mounted on rails 114, 116 with one pulley being positioned at each end of each rail. Pulleys 120, 122 are, in the preferred embodiment, mounted so that their axes of rotation are parallel to each other and perpendicular to the plane of the rails 114, 116. To avoid having cables 96, 97 which are placed around pulleys 120, 122 from coming into contact with bridge 62 or carriage 48, or both, translating, or power pulleys, 124*a, b, c, d* are mounted one at each end of rails 114, 116. The axes of rotation of pulleys 124 are parallel to each other and to the plane of rails 114, 116. The function of translating pulleys 124 are to lower the portion of the cables 96, 97 which run diagonally from the corners of the rails so that they pass under bridge 62. Pulleys 124 can also be used to apply power to move bridge 62 and carriage 48. One way of doing this is by motors 126*a, b* which can be conventional variable speed reversible dc servo motors.

One end of cable 96 is fastened securely to carriage 48. Cable 96 is then placed around pulleys 120*a*, 124*a*, 122*a*, 122*d*, 124*d*, 120*d* and its other end is secured to carriage 48 by a coil spring 127 to maintain tension on cable 96. Similarly cable 97, one end of which is secured to carriage 48, is placed around pulleys 120*b*, 124*b*, 122*b*, 122*c*, 124*c*, 120*c* and its other end is attached by coil spring 127 to carriage 48. The function of coil spring 127 is to maintain the proper tension on cables 96 and 97.

Figure 8:
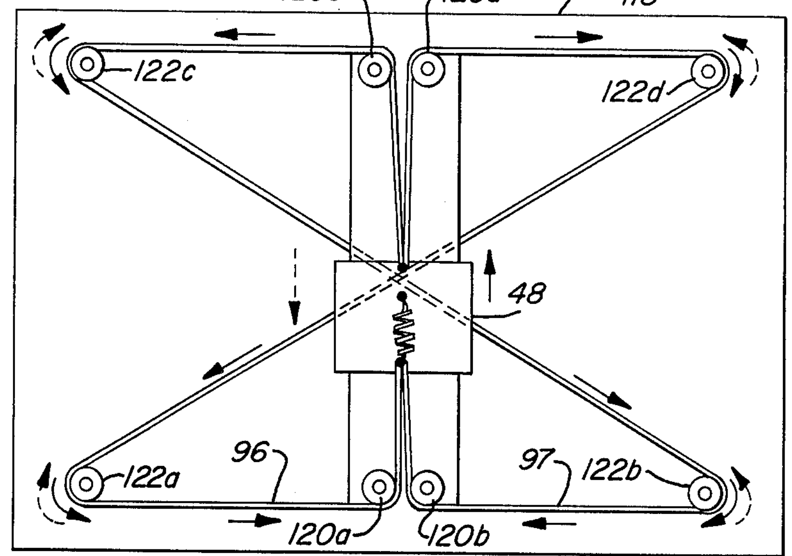
FIGS. 8 and 9 are schematic views of the transport mechanism of FIG. 7 which illustrate how the mechanism functions.
Figure 9:
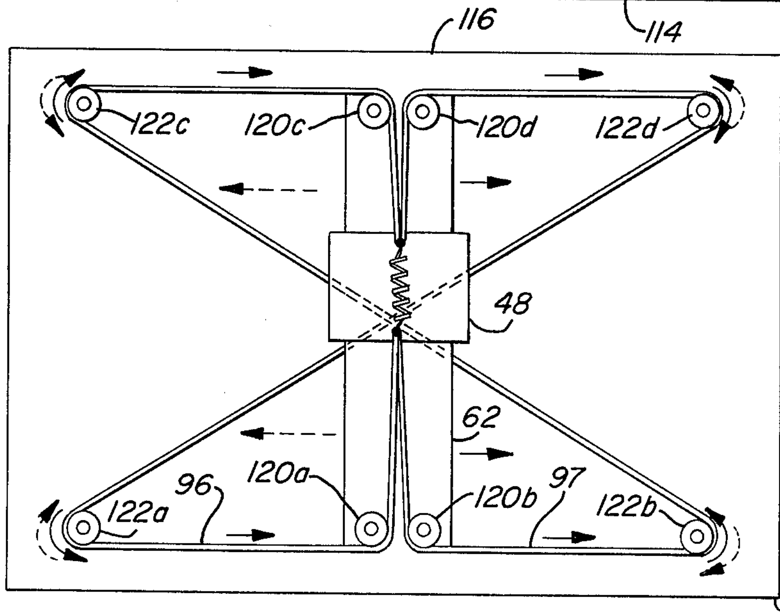

FIG. 8 and 9 illustrate schematically the theory of operation of transport mechanism 14. Translating pulleys 124 which are provided to avoid problems due to the thickness of the rails, truss and carriage are omitted to simplify the illustration. In FIG. 8 if power is applied to cables 96, 97 to cause pulleys 122*a*, 122*b*, which in FIG. 8 are the equivalent of the pulleys 122*a*, 122*b* and translating pulleys 124*a*, 124*b*, to rotate in opposite directions and if the direction of rotation is in the direction of the solid arrows, carriage 48 will move in the direction of the solid arrow toward rail 116. If pulleys 122*a, b* rotate in opposite directions as shown by the dashed line arrows of FIG. 8, carriage 48 will move in the direction of the dashed arrow toward rail 114.

FIG. 9 illustrates what happens if cables 96, 97 are driven to cause pulleys 122*a, b* to rotate in the same direction. If in the direction of the solid arrows then bridge 62 will move to the right as indicated by the solid arrows and if pulleys 122*a, b* rotate in the direction of the dashed line arrows, then bridge 62 will move to the left in the direction of the dashed arrows.

The motors which provide power to cables 96, 97, if they cause cables 96, 97 to move at the same speed, will cause either carriage 48 or bridge 62 to move depending upon the direction of movement of the cables but not both. If the speeds of cables 96, 97 are not the same, then both the carriage 48 and bridge 62 will move.

Transport mechanism 14 permits carriage 48 to be moved to any position substantially within the rectangular area 128 which is seen in FIG. 7, which area lies within lines tangent to the rail pulleys 122. Instead of providing power to the flexible cables 96, 97 by motors 126*a, b* driving pulleys 124*a, b,* power could be provided by flexible drive cables placed around drive pulleys 130*a, b* which are directly connected to translating pulleys 124*a, d* in the embodiment illustrated in FIG. 7 which drive cables may be powered by motors located outside of examination tank 50. Other ways of providing the power to the cables 96, 97 are possible and fall within the scope of this invention.

Orienting mechanism 68 of transport mechanism 14 orients the scanners 40, 42 so that they are optimally positioned with respect to a patient's breast to be scanned; i.e., so that the beams of acoustic energy produced by the ultrasonic transducers are as nearly perpendicular to the sides of the breast being scanned as possible. As described above, rotating pinion gear 74 will cause top member 69 of the four link flipping mechanism 69 to change the angle of link 69 with respect to vertical. To cause pinion gear 74 to rotate, track 114 is provided with a rack 132 substantially in the center of track 114 as illustrated schematically in FIG. 7. Referring to FIG. 10, pinion gear 74 has one end extended so that it projects beyond shoulder 76*a* which is mounted substantially at one end of bridge 62. Gear 134 is mounted on pinion gear 74 by a conventional slip clutch 136 so that the teeth of gear 134 will mesh with the teeth on rack 132. Thus as bridge 62 moves from right to left, as seen in FIG. 7, driving gear 134 will be caused to rotate in a counterclockwise direction which causes link 69 to change its orientation with the result that scanner 40 would be lower and scanner 42 will be higher. Moving bridge 62 from left to right would cause the flipping mechanism 68 to position the scanners as illustrated in FIG. 3. Since shaft 74 runs the full length of bridge 62, flipping mechanism 68 will work independently of the position of carriage 48 on bridge 62. Slip clutch 136 is provided so that if scanners 40, 42 are repositioned by hand, for example, so that arm 44 is in contact with adjustable stop 94 and bridge 62 is moved from right to left as described above, driving gear 134 will rotate, but the torque applied to pinion gear 74 will be sufficiently low as to not damage flipping mechanism 68.

Advantages of flipping mechanism 68 are that it provides an effective gear reduction, it takes only a short length of rack 132 to reorient the scanners. The orientation of the scanners 40, 42 is stable when drive gear 134 is no longer in contact with rack 132 since the center of gravity of the scanners has to be raised significantly to change their orientation. In addition, the four link flipping mechanism provides an essentially stable point for attaching the electrical conductors and compressed air lines to carriage 48 to minimize the length of such lines and conductors.

Figure 11:
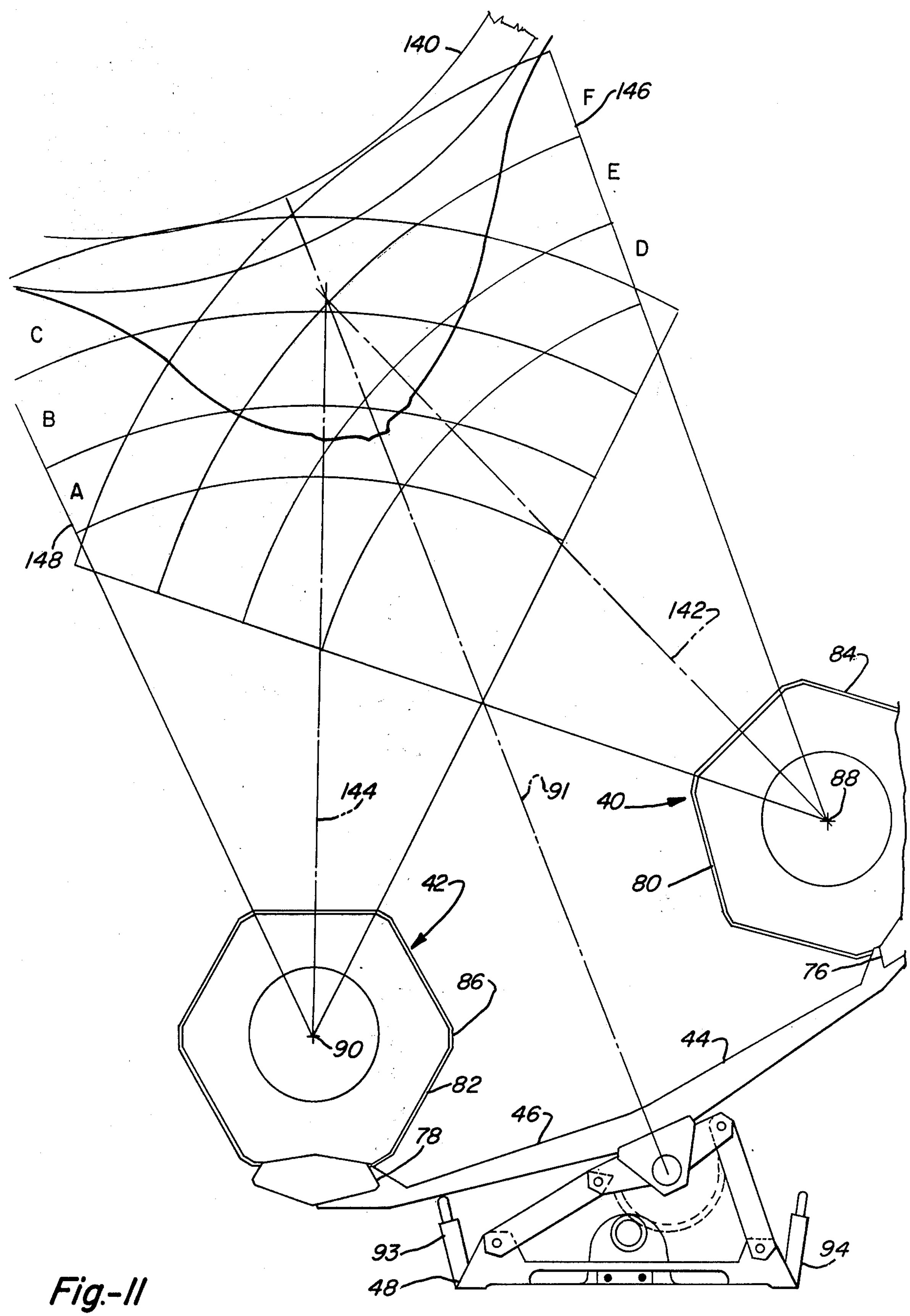
FIG. 11 is a partial front elevation showing the relationship of the ultrasonic scanners of the invention and a patient's breast which is to be scanned to produce a high resolution visualization of the tissue thereof.

To conduct an ultrasonic examination of a patient's breasts, or more specifically to produce a series of cross-sectional images of the tissue of each breast, the patient 60 lies prone on examination table 53 with her breasts 61 freely floating in the liquid with which examination tank 50 is filled, degassed water in the preferred example. The side walls of tank 50 as well as those of overflow tank 51, are transparent, or are provided with windows, so that the operator can properly position carriage 48 relative to the patient. Referring to FIG. 11 scanners 40, 42 are mounted on arms 44, 46 which in turn are mounted on carriage 48 of transport mechanism 14. In scanning the patient's left breast, for example, scanner 42 which is between the breasts is lower than scanner 40. The operator positions the carriage 48 so that the perpendicular bisector 91 substantially passes through the nipple of the patient and is also substantially perpendicular to the patient's rib cage 140. The scanning heads 84, 86 are positioned as illustrated in FIG. 11 so that the centerlines 142, 144 of the sector scans conducted by scanning heads 84, 86 intersect perpendicular bisector 91 at a point substantially directly behind the nipple and between the nipple and the rib cage 140. Carriage 48 is positioned on bridge 62 so that if scanning starts at the inferior border of the breast the carriage 48 will be moved along bridge 62 toward rail 116 at a constant speed until the superior border of the breast is scanned. Controls of the movement of carriage 48 is by controlling servo motors 16. Under overall control of the operator, control processor 26 in response to position information received from servo motors 16 causes a dc voltage to be supplied to the motors which is a function of the desired velocity of motors 16. Servo motors 16 control the direction of movement of flexible cables 96, 97 as described above and the speed of movement is of course determined by the speed at which the cables are driven.

When scanning subsystem 12 is properly positioned, motors 18*a,* 18*b* driving the scanning heads 84, 86 are energized. As described above, the motors 18*a,* 18*b* for scanners 40, 42 are, in the preferred embodiment, 3600 rpm synchronous motors which are geared down to rotate scanning heads 84, 86 at 100 rpm each. At this angular velocity heads 84, 86 produce no cavitation or extraneous noise which would interfere with the operation of transducers 20 or have an adverse effect on the resolution of the images produced. Transmitter/-receiver 24 is energized. To produce the overlapping sector scan illustrated in FIG. 11 while avoiding having more than one transducer 20 of either scanning head 84, 86 connected to transmitter/receiver 24 at the same time, it is necessary to maintain the phase angle $\gamma$ between the two scanning heads 84, 86 at the correct value for $\gamma$ which equals the central angle of one of the conductive arcs 107 during which the ultrasonic transducers connected to the arc is energized, i.e., substantially 60° plus 45° so that the angle $\gamma$ is 105° in the preferred embodiment.

Fiducial marks 106*a,* 106*b* are used to determine or measure $\gamma$ and are positioned so that they produce a signal or pulse each time the wiper arms 109*a,* 109*d* contact fiducial marks 106*a,* 106*b*. Knowing the angular velocity of scanning heads 84, 86, the angle $\gamma$ is then a function of the difference in time $\Delta t$ between wiper 109*a* contacting fiducial mark 106*a* and wiper 109*d* contacting fiducial mark 106*b*, for example. Computer controller 26 can measure $\Delta t$ and if $\Delta t$ does not have the right value, controller 26 causes one or the other of motors 18*a,* 18*b* to slow down momentarily, for example. One way of doing this would be to use a variable frequency oscillator to provide the power to motors 18*a,* 18*b* and by changing the frequency of the alternating current applied to one of the motors to produce the change necessary to obtain the desired phase angle $\gamma$. Another way is to momentarily interrupt the power supplied to one of the motors 18*a* or b by use of conventional solid state relays 22. Obviously motors 18*a* and 18*b* could also be variable speed dc motors so that the speed of one motor could be varied enough to produce the desired phase angle $\gamma$.

Once the scanning heads 84, 86 are properly synchronized with the proper phase angle $\gamma$, the scanning commences and the carriage 48 is caused to move by applying power to the flexible cables 96, 97 to cause them to move at controlled velocities. The velocity of the carriage 48 or bridge 62 is chosen so that it advances at a rate of from 1 to 2 millimeters per revolution of scanning head 84, for example. During each revolution of each scanning head 84, 86 each of the transducers 20*a–f* is connected to transmitter/receiver 24. Sectors 146, 148 scanned by the scanning heads 84, 86 respectively as illustrated in FIG. 11 are divided into three contiguous zones A, B, C of sector 148 and zones D, E, F of sector 146. The widths, or depths, of the sectors substantially correspond to the focal range of the transducer conducting the scan of the zone with some overlap at the common boundaries; for example the scan of zone A of sector 148 may be conducted by transducer 20*a* of scanning head 86. Similarly the scanning of different zones of each sector by different transducer 20 results in sector scans of higher resolution which sector scans are overlapped in the area of greatest interest with respect to the detection of tissue abnormalities in the breast.

The echoes received by each transducer 20*a–f* are converted by signal processor 28 from A mode to ultrasonic video signals which are applied to scan converter 30 as described above. The scan converter 30 converts the signals applied to it into video signals suitable for display on TV monitor 34 and for recording by a video recorder 36. The operator controls how the images produced from the echoes will be displayed. For example, the signals from each zone of each sector could be separately displayed. The signals from each scanning head can be displayed together to provide a sector scan or the signals can be combined to produce a composite image. Best resolution is obtained when the images of all zones of both sectors are combined to produce an overlapped, or composite, image or visualization. Resolution is also improved by operating the scan converter 30 in an integrating mode.

After carriage 48 is moved from the inferior to the superior border of the patient's left breast for example, the carriage is then moved by causing the bridge 62 to move until the scanning head 40 is between the breasts of the patient. As bridge 62 moves driving gear 134 will engage rack 132 mounted on rail 114 and rotate. Rotation of pinion gear 74 in a counterclockwise direction as viewed in FIG. 3 will change the orientation of top member 69 so that arm 44 engages adjustable stop 94. Once arm 44 engages stop 94, slip clutch 136 permits drive gear 134 to continue to rotate as long as it engages rack 132 without applying excessive torque to pinion gear 74.

The operator controls the position of bridge 62 so that the perpendicular bisector 91 will pass through the nipple of the patient's right breast, for example, and be substantially perpendicular to the patient's rib cage 140. It has been noted that lines through the nipples of each breast perpendicular to the rib cage, which lines are also the axes of symmetry of the breast, diverge generally at an angle of 45° to one another. To properly position scanners 40, 42 for patient's whose breasts diverge at substantially different angles, it is possible to adjust the angle that the perpendicular bisector 91 makes with vertical by changing the length of adjustable stops 93, 94.

Once bridge 62 is positioned so that the perpendicular bisector 91 will pass through the nipple of the patient's right breast and again be substantially perpendicular to the patient's rib cage 140 behind the second breast, carriage 48 is moved until it is at the inferior border of the breast. Then carriage 48 is caused to move toward the superior border at a constant rate of 1 to 12 millimeters per revolution of the scanning heads. A scan of the second breast is conducted in substantially the same way as the first.

In a preferred embodiment control processor 26 is a model 6502 made by the MOS Technology Company, scan converter 30 is a model 639H made by the Hughes Aircraft Company, TV display or monitor 34 is a model VF02 made by the Conrac Company, video recorder 36 is a model CR6060U made by the JVC Company and keyboard 38 is a model L1648 made by the Key-Tronic Company.

From the foregoing it is believed obvious that this invention provides an improved high resolution rotating head ultrasonic scanner which is particularly useful in a scanning subsystem for an ultrasonic breast scanner that provides visualizations of breast tissue of significantly improved resolution, which requires little time to conduct an examination, does not require a highly skilled operator and conducts the examination with the minimum of discomfort to the patient so that many patients can be examined to increase the probability of the early detection of breast carcinoma or precancerous conditions and thus to minimize the death rate from cancer of the breast.

It should be evident that various modifications can be made to the described embodiment without departing from the scope of the present invention.

What is claimed is:

1. An ultrasonic scanner comprising:

a body portion;

a scanning head having an axis of rotation;

means for mounting the scanning head on the body portion for rotation about its axis of rotation;

means mounted on said body portion for rotating the scanning head about its axis of rotation;

a plurality of wide apertured focused ultrasonic transducers, each transducer being individually distinct from said other transducers, each transducer having a predetermined focal range different than the predetermined focal ranges of each of said other transducers, said focal ranges being contiguous, each of said transducers when energized producing a beam of acoustic energy having a beam axis, each of the beams of acoustic energy being produced only by one of said distinct energized transducers;

means for mounting the transducers on the scanning head so that the beam axes of said transducers are substantially perpendicular to the axis of rotation of the scanning head, said beam axes substantially lying in the same plane, and the angles between the beam axes being substantially equal; and means for connecting the transducers to a transmitter/receiver and for energizing the transducers so that the transducers scan a given sector, said sector being divided into contiguous zones with the depth of each zone of the given sector corresponding to the focal range of one of the transducers.

2. The ultrasonic scanner of claim 1 in which the means for rotating the scanning head rotates the scanning head at a substantially constant angular velocity.

3. The ultrasonic scanner of claim 2 in which the number of ultrasonic transducers is three.

4. The ultrasonic scanner of claim 3 in which the angle scanned of the given sector is substantially 60°.

5. A scanning subsystem for an ultrasonic breast scanner comprising:

a pair of scanners, each scanner having a rotating scanning head, each scanning head having a perimeter;

means for causing the scanning heads to rotate at substantially the same angular velocity about their axes of rotation;

"n" ultrasonic transducers mounted on each scanning head, each transducer producing when energized a beam of acoustic energy having a beam axis, each transducer being a wide apertured focused transducer having a predetermined focal range, the focal ranges of the transducers of a scanning head not being the same, said transducers being substantially uniformly spaced around the perimeters of the scanning heads and so that the axes of beams of acoustic energy produced by the transducers when energized are substantially perpendicular to the axis of rotation of the scanning heads;

means for connecting the transducers of each scanning head to a transmitter/receiver so that one and only one transducer is energized by the transmitter/receiver at any one time, and so that each scanning head conducts a sector scan, the sector scanned by each scanning head being divided into "n" zones, each zone having a depth corresponding to the focal range of a different one of the transducers of a scanning head;

a transport mechanism;

means for mounting the scanners on the transport mechanism; and means for controlling the phase angle between the scanning heads of the scanners so that the phase angle has a predetermined value so that the sectors scanned by the scanning heads overlap.

6. The scanning subsystem of claim 5 in which "n" equals three.

7. The scanning subsystem of claim 6 in which the focal ranges of the transducers of a scanning head are contiguous.

8. The scanning subsystem of claim 5 in which the transport mechanism includes means for orienting the scanners so that the perpendicular bisector of a line between the axes of rotation of the scanning heads has a predetermined angle with respect to vertical.

9. The scanning subsystem of claim 8 in which the means for orienting the scanners includes a four-link flipping mechanism.

10. A scanning subsystem for an ultrasonic breast scanner comprising:

a transport mechanism including a movable carriage;

orienting means mounted on the carriage;

a pair of scanners, one scanner mounted on each arm, each scanner having a body and a scanning head mounted for rotation on said body about an axis of rotation, said axes of rotation being substantially parallel to each other;

"n" wide apertured focused transducers mounted on each scanning head where "n" is an integer greater than 1.

means for electrically connecting the transducers of each scanning head to a transmitter/receiver, each transducer when energized by the transmitter of the transmitter/receiver producing a beam of ultrasonic energy having a beam axis, and when connected to the receiver said transducers producing electrical signals which are a function of the intensity of the ultrasonic energy reflected back from a transmitted beam;

the "n" transducers of each scanning head being mounted so that the beam axis of each transducer lies in a plane of rotation substantially perpendicular to the axes of rotation of the scanning heads and so that the angle between the axes of the beams of the transducers mounted on a scanning head are substantially equal, each transducer of a scanning head having a different focal range;

means for rotating the scanning heads at substantially the same angular velocity and in the same direction;

means for causing the transducers of each scanning head to conduct a sector scan, each sector being divided into "n" zones with the depth of each zone corresponding to a focal range of one of the transducers of each scanning head; and means for controlling the phase angle between the scanning heads of the scanners so that sectors scanned by the scanning heads overlap.

11. The scanning subsystem of claim 10 in which "n" equals three.

12. The scanning subsystem of claim 11 in which the focal ranges of the transducers of a scanning head are contiguous.

13. The scanning subsystem of claim 10 in which the transport mechanism includes a pair of rails, a bridge movable on the rails, said movable carriage being mounted on the bridge, and means for moving the carriage and the bridge.

14. The scanning subsystem of claim 13 in which the means for moving the carriage and the bridge include pulleys mounted on the rails and bridge, a pair of flexible cables connected to the carriage and positioned on the pulleys, and means for applying force to the cables.

15. The scanning subsystem of claim 10 in which the orienting means positions the scanners so that the perpendicular bisector of a line between the axes of rotation of the scanning heads in the plane of rotation of the beam axes of the transducers of said heads has a predetermined angle with respect to vertical.

16. The scanning subsystem of claim 15 in which the orienting means includes a four-link flipping mechanism.

17. An improved method for visualizing the tissue of female breasts comprising the seps of:

immersing a patient's breast in a liquid filled container;

movably locating within the container a pair of scanners, each scanner having a rotating scanning head, each scanning head having a plurality of ultrasonic transducers, each transducer of each scanning head having a predetermined focal range different than the other transducers of said scanning head, the transducers of each scanning head having substantially contiguous focal ranges;

positioning the scanners so that the breast to be scanned is between them;

rotating the scanning heads at substantially the same angular velocity;

maintaining a predetermined phase angle between the rotating scanning heads;

connecting the transducers to a transmitter/receiver so that only one transducer is energized by the transmitter/receiver at any one time and one transducer is substantially continuously energized by the transmitter/receiver;

moving the scanners from one border to the other of the breast between; and producing visually observable images of the echoes received by the transducers.

18. The improved method of claim 17 in which the number of ultrasonic transducers on each scanning head is three.

19. An improved method for visualizing the tissue of the female breast comprising the steps of:

immersing a patient's breast in a liquid filled examination tank;

positioning a pair of scanners in the examination tank so that the breast to be scanned is between them, each scanning head having three wide apertured focused ultrasonic transducers, the focal ranges of the transducers of a scanning head being substantially contiguous;

connecting the ultrasonic transducers of the scanning heads to a transmitter/receiver so that each scanning head conducts a sector scan over an angle of substantially 60°, each sector being divided into three zones corresponding to the focal ranges of the transducers of a given scanning head;

controlling the phase angle of the rotating scanning heads so that the sectors scanned by the ultrasonic transducers of each scanning head overlap;

conducting an overlapped sector scan of the breast between the scanners from one border of the breast to the other; and producing cross-sectional images from the echoes received by the transducers.

20. The improved method of claim 19 comprising the additional step of recording the cross-sectional images.

21. An ultrasonic breast scanning system comprising:

an examination tank open at the top;

an overflow tank open at the top, said examination tank being mounted within the overflow tank;

an examination table overlying the examination and overflow tanks;

an examination opening in the examination table over the examination tank so that a patient can lie prone on the table and the patient's breasts can be immersed in the liquid with which the examination tank is adapted to be filled;

a drainage opening formed in the examination table over the overflow tank so that liquid escaping from the examination tank is collected in the overflow tank;

pump means for pumping liquid from the overflow tank into the examination tank to maintain the liquid level in the examination tank at its maximum height;

transport and orienting means mounted in the examination tank;

a pair of scanners mounted on the transport and orienting means;

each of said scanners having a rotating scanning head having an axis of rotation;

a plurality of ultrasonic transducers mounted on each scanning head, each transducer of a scanning head having a different focal range, each transducer producing when energized a beam of acoustic energy having a beam axis, said transducers being positioned on each scanning head so that the beam axes are substantially normal to the axis of rotation and lie in substantially the same plane of rotation;

means for energizing the transducers to produce acoustic energy, said means energizing only one transducer at a time;

means for orienting the scanners so that the perpendicular bisector of the line between the axes of rotation of the scanners lying in the plane of rotation passes through the nipple of the patient's breast to be scanned and is substantially normal to the patient's rib cage;

means for causing the scanners to conduct overlapping sector scans;

means for causing the transport mechanism to move the scanners from one border of the breast to be scanned to the other at a predetermined velocity;

means for converting the reflections of acoustic energy transmitted from and then received by a transducer into ultrasonic video signals; and means for displaying the ultrasonic video signals.

22. An ultrasonic breast scanning system as defined in claim 21 in which the capacity of the overflow tank is greater than that of the examination tank.

23. An ultrasonic breast scanning system as defined in claim 25 in which the number of ultrasonic transducers mounted on each scanning head is three.

24. An ultrasonic breast scanning system as defined in claim 23 in which the focal ranges of the transducers of each scanning head are contiguous.

25. An ultrasonic breast scanning system as defined in claim 21 in which the means for orienting the scanners include a four-link flipping mechanism.

26. An ultrasonic scanner for scanning an object, comprising:

a body portion;

a plurality of focused ultrasonic transducers, each transducer being individually distinct from said other transducers, each transducer having a predetermined focal range different than each of the predetermined focal ranges of said other transducers, said focal ranges being contiguous, each of said transducers when energized producing a beam of acoustic energy having a beam axis, each of the beams of acoustic energy being produced only by one of said distinct, energized transducers;

means for mounting said transducers on said body portion;

means for moving said body portion so that the object is scanned by said transducers; and means for connecting the transducers to a transmitter/receiver and for energizing said transducers so that said transducers scan a given sector, said sector being divided into contiguous zones with the depth of each zone of the given sector corresponding to the focal range of one of said transducers.

* * * * *

UNITED STATES PATENT AND TRADEMARK OFFICE

CERTIFICATE OF CORRECTION

PATENT NO. : 4,233,988

DATED : November 18, 1980

INVENTOR(S) : Donald E. Dick; Robert L. Metz; D. Scott RoJohn; Raymond D. Elliott It is certified that error appears in the above—identified patent and that said Letters Patent is hereby corrected as shown below:

Column 8, line 19, delete "more" and insert --move--.

Column 18, line 33, delete "25" and insert --22--.

Signed and Sealed this

*Third* Day of *March 1981*

[SEAL]

*Attest:*

RENE D. TEGTMEYER

*Attesting Officer* *Acting Commissioner of Patents and Trademarks*